United States Patent [19]

Kim et al.

[11] Patent Number: 5,756,731
[45] Date of Patent: May 26, 1998

[54] PROCESS FOR PREPARATION OF (−)3(S)-METHYLBENZOXAZINE DERIVATIVE

[75] Inventors: Youseung Kim; Soon Bang Kang; Eu Jin Ahn, all of Seoul, Rep. of Korea

[73] Assignee: Korea Institute of Science and Technology, Seoul, Rep. of Korea

[21] Appl. No.: 613,299

[22] Filed: Mar. 11, 1996

[30] Foreign Application Priority Data

Mar. 20, 1995 [KR] Rep. of Korea ............... 5780/1995

[51] Int. Cl.$^6$ ................................... C07D 265/36
[52] U.S. Cl. ........................................... 544/105
[58] Field of Search ............................... 544/105

[56] References Cited

FOREIGN PATENT DOCUMENTS

| 0368410 | 6/1989 | European Pat. Off. . |
| 322815 | 7/1989 | European Pat. Off. . |
| 368410 | 5/1990 | European Pat. Off. . |

OTHER PUBLICATIONS

Hayakawa et al., "Synthesis and Antibacterial Activities of Substituted 7-Oxo-2,3-dihydro-7H-pyrido[1,2,3-de][1,4]benzoxazine-6-carboxylic Acids," *Chem. Pharm. Bull.*, 4907–4913 (1984).

Atarashi et al., "Synthesis and Antibacterial Activities of Optically Active Ofloxacin and Its Fluoromethyl Derivative," *Chem. Pharm. Bull.*, 1896–1902 (1987).

Toshihiro et al., "Process for the Preparation of Benzoxazine Derivatives," *Chem. Abstr.*, 111:134170z (1989).

Toshihiro et al., "Preparation of (S)-3-alkyl-3,4-dihydro-2H-[1,4]benzoxazine Derivatives by Optical Resolution with N-(substituted sulfonyl-(R)-proline," *Chem. Abstr.* 112:35875x (Jul., 1989).

Hiroki et al., "Resolution of 7,8-dihalo-3-alkyl-3,4-dihydro-2H-[1,4]benzoxazines by HPLC," *Chem. Abstr.* 112:198397g (Oct., 1989).

Hiroki et al., "Optical Separation of (−)-3-alkyl-3,4-dihydro-2H-[1,4]-benzooxazines withi Bacteria," *Chem. Abstr.*, 113:76637K (1990).

*Primary Examiner*—John M. Ford
*Attorney, Agent, or Firm*—Townsend and Townsend and Crew

[57] ABSTRACT

A process for preparing (−)3(S)-methylbenzoxazine derivative of formula (I) comprising the steps of reacting the compound of formula (II) with benzoic acid, triphenylphosphine and diethyl azodicarboxylate in an organic solvent to obtain the compound of formula (III); hydrogenating the compound of formula (III) in the presence of a metallic catalyst to provide the compound of formula (IV); hydrolyzing the compound of formula (IV) to give the compound of formula (V); and reacting the compound of formula (V) with diethyl azodicarboxylate, triphenylphosphine, and zinc chloride in an organic solvent. The obtained (−)3(S)-methylbenzoxazine derivative is a useful intermediate for preparing an antibacterial agent which has a potent bacteriocidal effect.

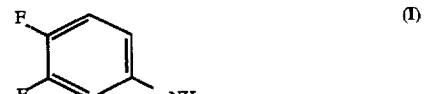

(I)

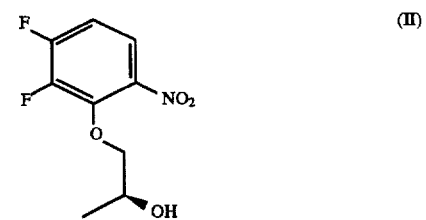

(II)

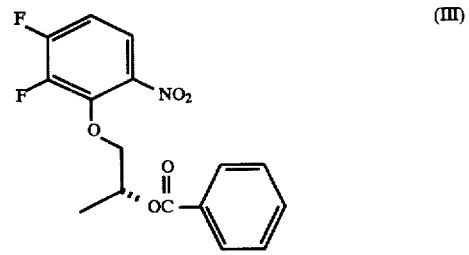

(III)

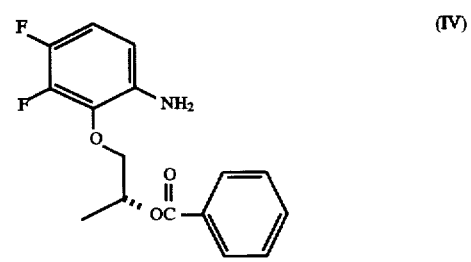

(IV)

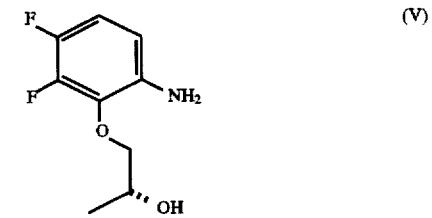

(V)

11 Claims, No Drawings

PROCESS FOR PREPARATION OF (−)3(S)-METHYLBENZOXAZINE DERIVATIVE

BACKGROUND OF THE INVENTION

1. Field of the Invention

The present invention relates to a process for preparation of (−)3(S)-methylbenzoxazine derivative of the following formula (I) which is a useful intermediate for producing a potent antibacterial agent.

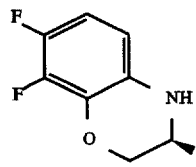

(I)

2. Description of the Background Art

Methods for preparing the aforementioned compound of formula (I) have been known for example, in European Patent Application Nos. 304,684, 322,815, and 368,410 and Japanese Laid-Open Publication Nos. 89-175,975, 89-261,380, 90-31,695, and 90-218,648. European Patent Application No. 304,684 and Japanese Laid-Open Publication No. 89-175,975 disclose a method in which a racemic 3-methylbenzoxazine derivative synthesized from 2,3,4-trifluoronitrobenzene compound is converted to a diastereomer and then separated as the compound of formula (I). Therefore, this method is lengthy and the resulted isomer has poor optical purity. Similarly, Japanese Laid-Open Publication Nos. 89-261,380 and 90-31,695 are not suitable for industrial or large-scale production since the separation of racemic 3-methylbenzoxazine compound prepared as aforementioned is carried out by using a chiral column or microorganisms. Also, the methods as disclosed in European Patent Application Nos. 322,815, 368,410, and Japanese Laid-Open Publication No. 90-218,648 have problems in that they employ 2,3-difluoro-6-nitrophenol and optically active, expensive compounds as starting materials and the purity of the isomers decreases during the reaction procedure.

SUMMARY OF THE INVENTION

Therefore, an object of the present invention is to provide a process for producing (−)3(S)-methylbenzoxazine derivative of formula (I) which serves as a useful intermediate for synthesizing an antibacterial agent which has a potent bacteriocidal effect.

The present inventors have intensively studied to provide a solution to the aforementioned problems of the prior arts and found a new method for preparing the compound of formula (I) with high purity and high yield in an economical process.

DETAILED DESCRIPTION OF THE INVENTION

The process for preparing (−)3(S)-methylbenzoxazine derivative of the structural formula (I) comprises reacting the compound of the following formula (II) with benzoic acid, triphenylphosphine, and diethyl azodicarboxylate in an organic solvent to obtain a pure isomer of the compound of the following formula (III), and reducing the compound of formula (III) to obtain the compound of the following formula (IV) which is then hydrolyzed to provide the compound of the following formula (V) and reacting the compound of formula (V) with diethyl azodicarboxylate, triphenylphosphine, and zinc chloride in an organic solvent.

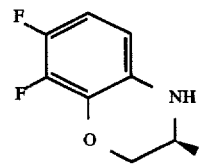

(I)

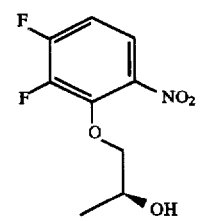

(II)

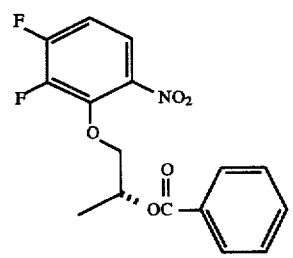

(III)

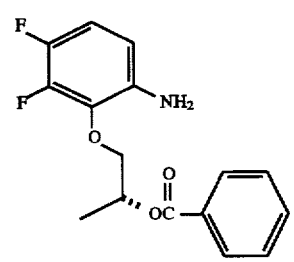

(IV)

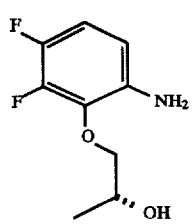

(V)

An exemplary reaction procedure for obtaining antibiotic agents from the compound of formula (I) is described as follows.

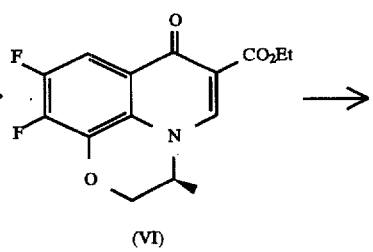

(VI)

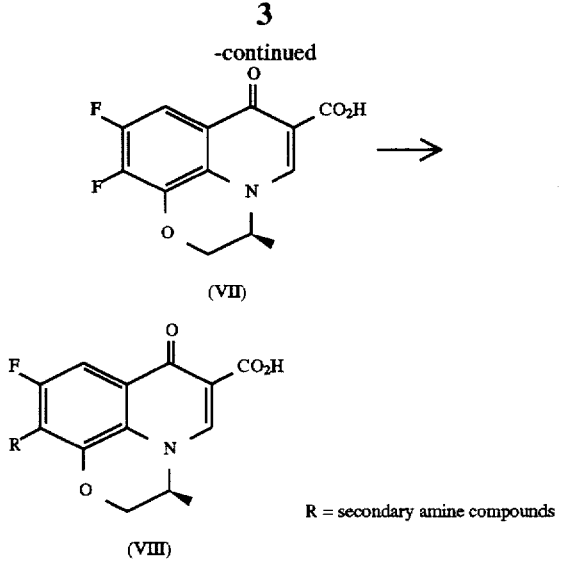

(VII)

(VIII)  R = secondary amine compounds

The strong bacteriocidal effect of the compound of formula (VIII) wherein R is substituted with N-methylpiperazine has been well known in for example, Chem. Pharm. Bull., 35, 1896–1902 (1987). The compound of formula (VI) which is prepared from the compound of formula (I) by using diethyl ethoxymethylenemalonate and polyphosphoric ester is then hydrolyzed under an acidic or alkaline condition to obtain the compound of formula (VII) and a suitable secondary amine compound is added thereto for obtaining the compound of formula (VIII). Such preparation method is described in Chem. Pharm. Bull. 32, 4907–4913 (1984).

A detailed description of the process according to the present invention is provided below.

The production method of the compound of formula (II) which is used as a starting material in the present invention is described in Korean Patent Application No. 94-22095 filed on Sep. 2, 1994, incorporated herein by reference.

(−)3,4-difluoro-2-(2-benzoyloxypropoxy)nitrobenzene of formula (III) is obtained by stirring the compound of formula (II) together with triphenylphosphine, benzoic acid and diethyl azodicarboxylate in an organic solvent at the temperature range of 5° to 100° C. for 1 to 4 hours. The organic solvent used can be for example, acetonitrile, diethyl ether, tetrahydrofuran, benzene or toluene.

The equivalent ratio of the compound of formula (II) to benzoic acid to triphenylphosphine to diethyl azodicarboxylate is preferably 1:1.2:1.5:1.5. The measurement of the optical activity of the compound of formula (III) shows an inversion and the compound of formula (III) is confirmed as (R) isomer.

Upon reacting the compound of formula (III) in the presence of a catalyst such as palladium, palladium hydroxide, platinum, and platinum oxide in a polar solvent such as tetrahydrofuran, acetonitrile, methanol, or ethanol under 1 atm. of hydrogen for 2 to 8 hours, the compound of formula (IV) is obtained. The weight ratio of the compound of formula (III) to the catalyst is preferably 10:1 or 20:1.

The compound of formula (V) is obtained by stirring the compound of formula (IV) together with an alkaline metal cyanide such as potassium cyanide or sodium cyanide in a polar solvent such as methanol or ethanol at the temperature range of 0° to 50° C. for 1 to 2 days, wherein the equivalent ratio of the compound of formula (IV) to alkaline metal cyanide is preferably 1:1.05 or 1:1.1.

Alternatively, the compound of formula (V) can also be obtained by stirring the compound of formula (IV) with an alkaline metal hydroxide such as potassium hydroxide or sodium hydroxide in a mixture of water and an alcohol such as ethanol or methanol at 20° to 80° C. for 1 to 4 hours. The volume ratio of water to alcohol is preferably 5:1 or 3:1.

Finally, the compound of formula (V) is heated with stirring at 50°–500° C. for 1 to 4 hours in the presence of triphenylphosphine, diethyl azodicarboxylate, and zinc chloride in an organic solvent to obtain the object compound of formula (I). The organic solvent which is used in this step can be selected from acetonitrile, tetrahydrofuran, diethyl ether, benzene or toluene. The equivalent ratio of the compond of formula (V) to diethyl azodicarboxylate to triphenylphosphine to zinc chloride is preferably 1:3:3:3.

The resulted compound can be separated and purified by using conventional methods such as evaporation, filtration, extraction, chromatography, distillation or any combination of these methods. For example, the reaction mixture can be concentrated to dry under reduced pressure and the residue is stirred in a mixture of water and an organic solvent such as methylenechloride, chloroform, diethyl ether or ethyl acetate and which is then concentrated. If by-products are present in the object compound, further purification can be carried out for obtaining the desired product by resorting to conventional techniques such as chromatography, redistillation or recrystallization.

A better understanding of the present invention may be obtained in light of following examples which are set forth to illustrate, but are not to be construed to limit the present invention.

EXAMPLE I

Preparation of (R) (−)-3 4-difluoro-2-(2-benzoyloxyropoxy)nitrobenzene (III)

1.59 g (6.82 mmol) of the compound of formula (II), 2.68 g (10.22 mmol) of triphenylphosphine and 1.0 g (8.19 mmol) of benzoic acid were added to 20 ml of benzene and cooled to 5° C. To this mixture, while stirring, 1.78 g (10.22 mmol) of diethyl azodicarboxylate was slowly added dropwise at 5° C. After stirring the reaction mixture at 25° C. for 1 hour, the solid product was filtered. The filtrate was removed under reduced pressure (25° C./20 mm Hg) and the residue was purified by silica gel chromatography (hexane:ethyl acetate=15:1 (volume ratio)) to give the titled compound (2.18 g, 95% yield).

m.p.: 44.5°–45.2° C.

$[\alpha]^{21}_D$ −19.2° (C=1.0, CHCl$_3$)

$^1$H NMR(CDCl$_3$) ppm: 8.01–8.03(2H, m), 7.66(1H, ddd, J=2.5H, 5.3H, 9.4H), 7.53–7.58(1H, m), 7.4–7.46(2H, m), 6.94–7.03(1H, m), 5.47–5.57(1H, m), 4.41–4.50(2H, m), 1.51(3H, d, J=6.6H)

IR(KBr) cm$^{-1}$: 1710, 1538, 1352, 1284

MS: 77(28), 105(100), 163(33), 186(0.3), 215(M$^+$)

Elemental analysis for C$_{16}$H$_{13}$N$_1$O$_5$F$_2$: Calculated: C, 56.98; H, 3.88; N, 4.15 Found: C, 56.80; H, 3.83; N, 3.86

EXAMPLE 2

Preparation of (R) (−)-3,4-difluoro-2-(2-benzoyloxypropoxy)aniline(IV)

1.50 g (4.44 mmol) of the compound (III) prepared in Example 1 and 1.5 g of 10% palladium/active carbon were added to 40 ml of tetrahydrofuran and reacted under 1 atm of hydrogen for 5 hours. Precipitate was filtered and the filtrate was removed under reduced pressure (25° C./20 mmHg) to give the titled, compound, an oily product (1.31 g, 96% yield).

$[\alpha]^{25}_D$ −48.4° (C=1.0, CHCl$_3$)

$^1$H NMR(CDCl$_3$) ppm: 8.04(2H, m), 7.57(1H, m), 7.44 (2H, m), 6.67(1H, m), 6.32(1H, ddd, J=2.2H, 4.8H, 8.8H), 5.47–5.57(1H, m), 4.24–4.32(2H, m), 3.74 (2H, brs), 1.45 (3H, d, J=6.3H)

IR(KBr) cm$^{-1}$: 3472, 3374, 1718, 1508, 1276

MS: 77(32), 105(100), 144(8), 163(50), 307(M$^+$)

Elemental analysis for C$_{16}$H$_{15}$N$_1$O$_3$F$_2$: Calculated: C, 62.53; H, 4.93; N, 4.55 Found: C, 62.45; H, 4.86; N, 4.51

EXAMPLE 3

Preparation of (R) (−)-3,4-difluoro-2-(2-hydroxypropoxy)aniline(V)

0.995 g (3.24 mmol) of the compound (IV) prepared in Example 2 and 0.22 g (3.38 mmol) of potassium cyanide were added to 25 ml of absolute methanol and stirred at 25° C. for 24 hours. The reaction mixture was removed under reduced pressure (25° C./20 mmHg) and the residue was purified by silica gel chromatography (hexane:ethyl acetate= 4:1 (volume ratio)) to give the titled compound, a solid product (0.645 g, 98% yield).

m.p. : 51.5° C.

$[\alpha]^{25}_D$ −37.0° (C=1.0, CHCl$_3$)

$^1$H NMR(CDCl$_3$) ppm: 6.68–6.77(1H, m), 6.42(1H, ddd, J=2.3H, 4.9H, 9.0H), 4.02–4.19(2H, m), 2.75–3.92(4H, m), 1.21 (3H, d, J=6.3H)

IR(KBr) cm$^{-1}$: 3380, 3318, 1510, 1490, 1050

MS: 145(100), 203(M$^+$)

Elemental analysis for C$_9$H$_{11}$F$_2$N$_1$O$_2$: Calculated: C, 53.20; H, 5.46; N, 6.89 Found: C, 53.15; H, 5.50; N, 7.15

EXAMPLE 4

Preparation of (R) (−)-3,4-difluoro-2-(2-hydroxypropoxy)aniline(V)

0.65 g (2.1 mmol) of the compound of formula (IV) prepared in Example 2 and 0.16 g (4 mmol) of sodium hydroxide were added to a mixture of 5 ml of water and 15 ml of methanol and stirred at 80° C. for 2 hours. The reaction mixture was removed under reduced pressure (25° C./20 mmHg) and the residue was purified by silica gel chromatography (hexane:ethyl acetate=4:1 (volume ratio)) to give the titled compound, a solid product (0.35 g, 82% yield).

EXAMPLE 5

Preparation of (S) (−)-7,8-difluoro-2,3-dihydro-3-methyl-4H-1,4-benzoxazine(I)

0.10 g (0.54 mmol) of the compound (V) prepared in Example 3 or Example 4, 0.425 g (1.62 mmol) of triphenylphosphine, 0.221 g (1.62 mmol) of zinc chloride were added to 5 ml of acetonitrile and cooled to 5° C. To this mixture, 0.282 g (1.62 mmol) of diethyl azodicarboxylate was slowly added dropwise and the resulted reaction mixture was stirred under heat for 1 hour, and then cooled to room temperature. The resulted solid was filtered and the filtrate was removed under reduced pressure (25° C./20 mmHg). The residue was purified by silica gel chromatography (hexane:ethyl acetate 6:1 (volume ratio)) to give the titled compound as an oily product (0.081 g, 81% yield).

$[\alpha]^{22}_D$ −5.29° (C=1.7, CHCl$_3$)

$^1$H NMR(CDCl$_3$) ppm: 6.55(1H, m), 6.25(1H, ddd, J=2.3H, 4.7H, 8.9H), 4.28(1H, dd, J=2.7H, 10.4H), 3.78(1H, dd, J=8.3H, 10.4H), 3.45–3.55(1H, m), 1.20 (3H, d, J=6.3H)

Other features, advantages and embodiments of the present invention disclosed herein will be readily apparent to those exercising ordinary skill in the art after reading the foregoing disclosures. In this regard, while specific embodiments of the invention have been described in detail, variations and modifications of these embodiments can be effected without departing from the spirit and scope of the present invention as described and claimed.

What is claimed is:

1. A process for preparing a (−)3(S)-methylbenzoxazine derivative of the following formula (I) comprising the steps of;

(a) reacting the compound of formula (II) with benzoic acid, triphenylphosphine, and diethyl azodicarboxylate in an organic solvent selected from the group consisting of acetonitrile, diethyl ether, tetrahydrofuran, benzene and toluene, at a temperature range of 0° C. to 30° C. for 1 to 4 hours to obtain the compound of following formula (III), (b) hydrogenating the compound of formula (III) in the presence of a metallic catalyst to obtain the compound of following formula (IV), (c) hydrolyzing the resulting compound of formula (IV) with an alkali metal cyanide or an alkali metal hydroxide in an alcoholic solvent to provide the compound of following formula (V), and (d) reacting the compound of formula (V) with diethyl azodicarboxylate, triphenylphosphine, and zinc chloride in an organic solvent to give the object compound of (−)3(S)-methylbenzoxazine derivative of formula (I).

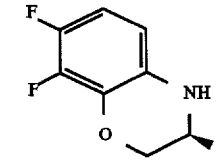

(I)

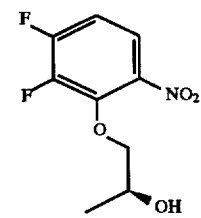

(II)

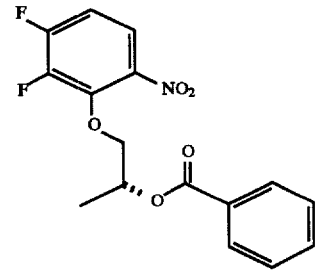

(III)

-continued

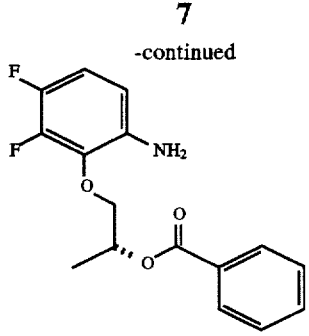
(IV)

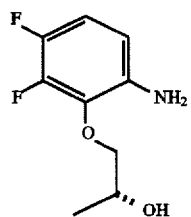
(V)

2. The process according to claim 1, wherein the hydrolysis of the step (c) for obtaining the compound of formula (V) is carried out by reacting the compound of formula (IV) with an alkaline metal cyanide in an alcoholic solvent.

3. The process according to claim 2, wherein the alkaline metal cyanide is sodium cyanide or potassium cyanide.

4. The process according to claim 1, wherein the hydrolysis of the step (c) is carried out at a temperature range of 0° to 50° C. for 24 to 48 hours.

5. The process according to claim 2, wherein the hydrolysis of the step (c) is carried out at a temperature range of 0° to 50° C. for 24 to 48 hours.

6. The process according to claim 1, wherein the hydrolysis of the step (c) for obtaining the compound of formula (V) is carried out by reacting the compound of formula (IV) with an alkaline metal hydroxide in a mixture of an alcohol and water.

7. The process according to claim 6, wherein the alkaline metal hydroxide is potassium hydroxide or sodium hydroxide.

8. The process according to claim 6, wherein the hydrolysis of the step (c) is carried out at a temperature range of 20° to 80° C. for 1 to 4 hours.

9. The process according to claim 2, wherein the alcohol is methanol or ethanol.

10. The process according to claim 6, wherein the alcohol is methanol or ethanol.

11. The process according to claim 1, wherein the final step (d) for obtaining the object compound of formula (I) is carried out at a temperature range of 50° to 100° C. for 1 to 4 hours.

* * * * *